US010119146B2

(12) United States Patent
Tsuchida et al.

(10) Patent No.: US 10,119,146 B2
(45) Date of Patent: *Nov. 6, 2018

(54) HIGHLY EFFICIENT ETHANOL-FERMENTATIVE YEAST

(71) Applicant: HONDA MOTOR CO., LTD., Tokyo (JP)

(72) Inventors: Yoshiki Tsuchida, Saitama (JP); Norihiko Tsukagoshi, Saitama (JP); Ikumi Kurihara, Saitama (JP); Kosuke Murata, Saitama (JP)

(73) Assignee: HONDA MOTOR CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/532,801

(22) PCT Filed: Dec. 5, 2014

(86) PCT No.: PCT/JP2014/082331
§ 371 (c)(1),
(2) Date: Jun. 2, 2017

(87) PCT Pub. No.: WO2016/088274
PCT Pub. Date: Jun. 9, 2016

(65) Prior Publication Data
US 2017/0342425 A1    Nov. 30, 2017

(51) Int. Cl.
| | | |
|---|---|---|
| *C12N 15/81* | (2006.01) | |
| *C12N 1/16* | (2006.01) | |
| *C12P 7/06* | (2006.01) | |
| *C12N 1/20* | (2006.01) | |
| *C12R 1/84* | (2006.01) | |
| *C12R 1/645* | (2006.01) | |

(52) U.S. Cl.
CPC ............. *C12N 15/815* (2013.01); *C12N 1/20* (2013.01); *C12P 7/06* (2013.01); *C12P 7/065* (2013.01); *C12R 1/645* (2013.01); *C12R 1/84* (2013.01); *Y02E 50/17* (2013.01)

(58) Field of Classification Search
None
See application file for complete search history.

(56) References Cited

U.S. PATENT DOCUMENTS

2013/0189788 A1    7/2013  Zhang et al.
2017/0369906 A1*  12/2017  Tsuchida .................. C12P 7/06

FOREIGN PATENT DOCUMENTS

| JP | 2011-050359 | 3/2011 |
| JP | 2012-170422 | 9/2012 |
| JP | 2014-158437 | 9/2014 |

OTHER PUBLICATIONS

Han Li-Li et al., "Breeding of Higher Ethanol Fermentation of Xylose Strain with Protoplast Fusion and Mtagenisis", Liquor Making, vol. 35, No. 2, Mar. 2008, 1002-8110 (2008), 02-0038-04, pp. 38-41, 4 pages, Beijing, China (English abstract included).
Chao Fan et al., "Efficient ethanol production from corncob residues by repeated fermentation of an adapted yeast", Bioresource Technology 136 (2013), pp. 309-315, Shanghai, China (English text), listed in International Search Report.
Itsuki Watanabe et al., "Ethanol production by repeated-batch simultaneous saccharification and fermentation (SSF) of alkali-treated rice straw using immobilized *Saccharomyces cerevisiae* cells", Bioresource Technology 123 (2012), pp. 695-698, Kanagawa, Japan, English text, listed in International Search Report.
Paul A. Bicho et al., "Induction of Xylose Reductase and Xylitol Dehydrogenase Activities in Pachysolen tannophilus and Pichia stipitis on Mixed Sugars", Applied and Environmental Microbiology, Jan. 1988, vol. 54, No. 1, pp. 50-54, 5 pages, English text, discussed in specification.
Min Zhang et al., "Metabolic Engineering of a Pentose Metabolism Pathway in Ethanologenic Zymomonas mobilis", ResearchGate, Article in Science Feb. 1995, Reprint Series, Jan. 13, 1995, vol. 267, pp. 240-243, 6 pages, English text, discussed in specification.
Angela Cristina Schirmer-Michel et al., "Production of ethanol from soybean hull hydrolysate by osmotolerant Candida guilliermondii NRRL Y-2075", ScienceDirect, Bioresource Technology 99 (2008), pp. 2898-2904, 7 pages, English text.
International Search Report, dated Mar. 17, 2015 (Mar. 17, 2015), 2 pages.

* cited by examiner

*Primary Examiner* — Channing S Mahatan
(74) *Attorney, Agent, or Firm* — Rankin, Hill & Clark LLP

(57) ABSTRACT

Provided is a highly efficient ethanol-fermentative yeast having high efficiency in ethanol production without introducing a foreign gene. The highly efficient ethanol-fermentative yeast is a fermentative yeast that effectively produces ethanol from pentose and hexose and is deposited to NITE Patent Microorganisms Depositary under the accession number NITE BP-01962.

2 Claims, 4 Drawing Sheets

HIGHLY EFFICIENT ETHANOL-FERMENTATIVE YEAST

TECHNICAL FIELD

The present invention relates to yeast for fermenting a saccharified solution in bioethanol production using lignocellulosic biomass.

In particular, the present invention relates to yeast capable of effectively producing ethanol from pentose (which may be, hereinafter, referred to as C5 sugar) and hexose (which may be, hereinafter, referred to as C6 sugar) in bioethanol production using lignocellulosic biomass.

BACKGROUND ART

Bioethanol is expected to be renewable, non-depletable resource that is produced by biomass. Moreover, since carbon dioxide that is produced by combustion of bioethanol is carbon neutral, increased use of bioethanol is considered to suppress increase of carbon dioxide, which is a main cause of the global warming.

Bioethanol is obtained by fermenting biomass and distilling and purifying ethanol. It is necessary to produce much alcohol from saccharified solutions for increasing the yield of bioethanol. Since the yeasts generally used in the process of bioethanol production cannot convert pentose such as xylose and arabinose into alcohol, only hexose has been used as raw materials for fermentation.

Typical biomass is reported to contain 35-45% of cellulose, 25-40% of hemicellulose, and 15-30% of lignin, though the contents vary according to raw materials. Therefore, use of hemicellulose, which mainly contains the pentose xylose, but not only cellulose, which is a polymer of hexose, as a substrate should lead to effective ethanol production.

Xylose is reported to be the second abundant sugar in biomass next to glucose and it is an important object in bioethanol production to use pentose effectively.

Techniques for using xylose, even at a little amount, by imparting the ability to utilize xylose by genetic recombination, using microorganism that produces ethanol from xylose, or the like have been so far disclosed.

Patent Literature 1 discloses an invention involving gen introduction having xylose transporter activity into hose cell to convert xylose (C5 sugar) into xylulose, which is incorporated in the pentose phosphate pathway of the glycolysis and use it for fermentation.

Patent Literature 2 discloses a technique for producing alcohol with yeast provided with an arabinose transporter. This involves incorporation of arabinose (C5 sugar) via arabitol and xylulose in the pentose phosphate pathway in the glycolysis to use it for fermentation, similar to the invention of Patent Literature 1.

Non Patent Literature 1 discloses provision of xylose utilization ability by incorporating a xylose utilization gene derived from *Escherichia coli* in *Zymomonas*.

Non Patent Literature 2 describes production of ethanol from xylose by yeast in the genus *Pichia*.

CITATION LIST

Patent Literature

Patent Literature 1:
Japanese Patent Laid-Open No. 2012-170422
Patent Literature 2:
U.S. Patent Application Publication No. 2013/189788

Non Patent Literature

Non Patent Literature 1:
Zhang, M., et al., Science, 1995. Vol. 267, pp. 240-243.
Non Patent Literature 2:
Bicho, P. A., et al., Appl. Environ. Microbiol., 1988, Vol. 54, pp. 50-54.

SUMMARY OF INVENTION

Technical Problem

However, the invention of Patent Literature 1 involves introducing a protein having the xylose transporter activity derived from *Candida guilliermondii* into *Saccharomyces cerevisiae* as a host. Accordingly, a foreign gene would be introduced. The invention of Patent Literature 2 is also an invention involving introduction of a gene from a species different from the host, although the transporter gene is different.

The technique described in Non Patent Literature 1 also involves introduction of a xylose utilization gene. The technical concept thereof is different from Patent Literature 1 and 2 described above, but they are similar in that a foreign gene is introduced.

Therefore, any of the inventions described in Patent Literature 1 and 2 and Non Patent Literature 1 requires adopting a containment measure to comply with "the Cartagena Protocol on Biosafety to the Convention on Biological Diversity" adopted in the United Nations. Accordingly, they require facilities for ensuring the biosafety and therefore it is disadvantageous in cost to produce ethanol using such microorganisms.

Moreover, use of yeast in the genus *Pichia* by the technique described in Non Patent Literature 2 does not result in much higher efficiency of ethanol production because of the low xylose usage ability of wild-type *Pichia* yeast.

An object of the present invention is to obtain a fermentation yeast with high efficiency of ethanol production without introducing a foreign gene.

Solution to Problem

To achieve the aforementioned object, a highly efficient ethanol-fermentative yeast according to the present invention is a fermentative yeast effectively producing ethanol from pentose and hexose and being deposited to NITE Patent Microorganisms Depositary under the accession number NITE BP-01962.

The wild-type *Meyerozyma guilliermondii* has a xylose utilization ability in addition to glucose utilization ability. However, it does not have sufficient ability to utilize xylose for the bioethanol production. In contrast, the highly efficient ethanol-fermentative yeast according to the present invention (which may be, hereinafter, also referred to as strain BP-01962) is yeast obtained by performing strain improvement using the strain N of *Meyerozyma guilliermondii* as a parent strain and selecting yeast having a high xylose utilization efficiency.

As a result, the highly efficient ethanol-fermentative yeast according to the present invention can have ethanol production efficiency higher than the parent strain without introducing a foreign gene.

The highly efficient ethanol-fermentative yeast according to the present invention has ethanol fermentation performance improved by performing habituation of the strain N of *Meyerozyma guilliermondii* in culture in a medium in which a mutagen is added to an enzymatically saccharified liquid derived from rice straw treated with ammonia and selecting yeast growing in the medium.

BRIEF DESCRIPTION OF DRAWINGS

FIG. 1 is a graph illustrating xylose utilization and ethanol yield in which FIG. 1A illustrates strain N and FIG. 1B illustrates strain BP-01962.

DESCRIPTION OF EMBODIMENTS

Figure 1:
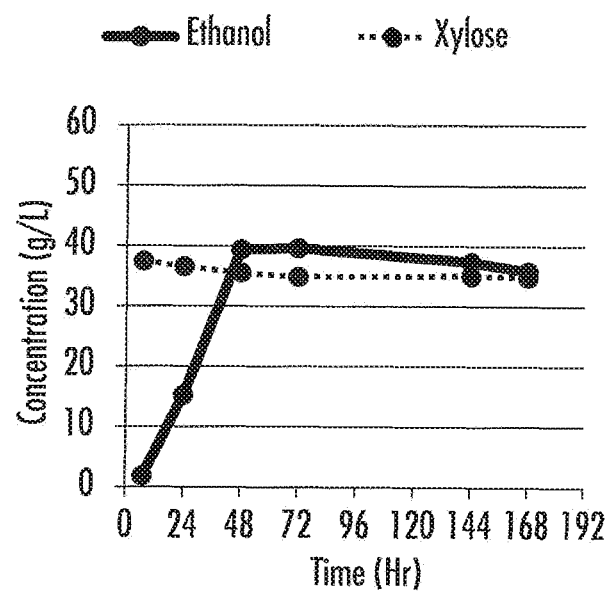
Figure 1:
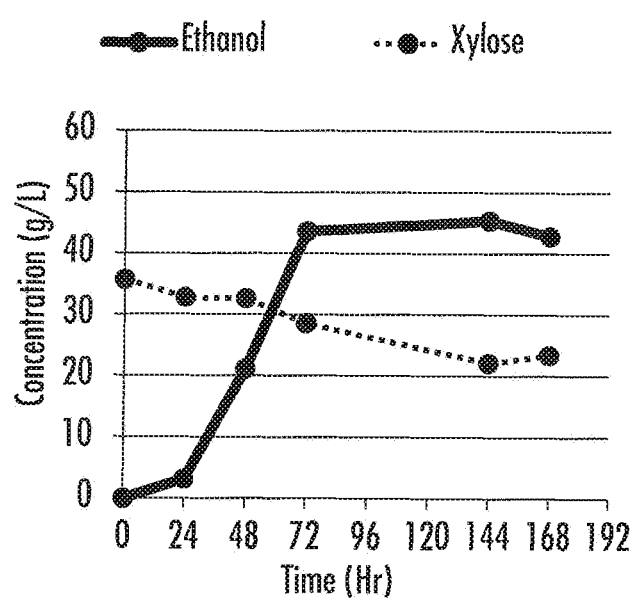

Next, embodiment of the present invention is further described in detail, referring to accompanying drawings.

The wild type of the *Ascomycete* yeast *Meyerozyma guilliermondii* possesses xylose utilization ability in addition to glucose utilization ability. However, the ability to utilize xylose thereof is not considered to be sufficient for the bioethanol production. Therefore, a highly efficient ethanol-fermentative yeast according to the embodiment is a mutant strain obtained by performing habituation using the strain N of the *Ascomycete* yeast *Meyerozyma guilliermondii* as a parent strain in culture in a medium in which a mutagen is added to an enzymatically saccharified liquid derived from rice straw treated with ammonia and selecting yeast growing in the medium.

The highly efficient ethanol-fermentative yeast according to the embodiment was deposited to NITE Patent Microorganisms Depositary (#122, 2-5-8 Kazusakamatari, Kisarazu-shi, Chiba 292-0818, Japan), National Institute of Technology and Evaluation (Independent Administrative Institution) by the applicant. The accession date is Nov. 19, 2014 and the accession number is NITE BP-01962. Hereinafter, the highly efficient ethanol-fermentative yeast according to the embodiment may be referred to as strain BP-01962.

Examples of the aforementioned enzymatically saccharified liquid derived from rice straw treated with ammonia that can be used include the one obtained as follows. Rice straw from Kumagaya-shi, Saitama, Japan was pretreated by immersing it in an equal amount of a 25 mass % ammonium solution at a temperature of 30° C. for 3 hours and then ammonia was evaporated. Next, after pH adjustment, a saccharification enzyme (manufactured by Meiji Seika Pharma Co., Ltd., trade name: Acremonium cellulose) was added to the pretreated rice straw and enzymatic saccharification was conducted with maintaining temperature at 50° C. for 72 hours to obtain a slurry containing an enzymatically saccharified liquid. Then, solid-liquid separation of the slurry was conducted by filter-pressing to collect a liquid as the aforementioned enzymatically saccharified liquid derived from rice straw treated with ammonia. The enzymatically saccharified liquid derived from rice straw treated with ammonia contains, for example, 3-15 mass % of glucose and 1-10 mass % of xylose.

Examples of the mutagen that can be used include ethylating agents such as N-ethyl-N-nitrosourea (ENU) and ethyl methanesulfonate (EMS), base analogs such as 5-bromo-2'-deoxyuridine (BrdU), and nitroso compounds such as nitroamine and nitrosoguanidine.

The strain BP-01962, the highly efficient ethanol-fermentative yeast of this embodiment is a mutant obtained by habituation of the aforementioned parent strain in culture in the aforementioned medium in which a mutagen is added to an enzymatically saccharified liquid derived from rice straw treated with ammonia and repeated selection of yeasts growing in the medium. Therefore, the strain BP-01962 has xylose utilization and ethanol fermentation performance improved in comparison with the wild type strain or the strain N of *Meyerozyma guilliermondii* without introducing a foreign gene.

Next, xylose utilization and ethanol yield of strain BP-01962 and the strain N of *Meyerozyma guilliermondii* were compared.

Liquid culture of the strain N of *Meyerozyma guilliermondii* was added to a synthetic medium at pH 4.7 containing 97.6 g/L of glucose, 41.5 g/L of xylose, 10.0 g/L of yeast extract, 20.0 g/L of peptone to obtain an $OD_{600}$ of 2.0 and cultured at a temperature of 30° C. for 168 hours. The medium was collected at predetermined time points and the concentrations of glucose and xylose were measured by HPLC (manufactured by Tosoh Corporation, trade name: LC-8020) and the concentration of ethanol by GC-FID (manufactured by GL Sciences Inc., trade name: GC390B). The results of the measurement of xylose concentration and the ethanol concentration are shown in FIG. 1A.

Next, an enzymatically saccharified liquid derived from rice straw treated with 26 mass % ammonia was used as a medium. A liquid culture of the strain BP-01962 was added to the medium to obtain an $OD_{600}$ of 2.0 and cultured at a temperature of 30° C. for 168 hours. The enzymatically saccharified liquid derived from rice straw treated with ammonia contained 112 g/L of glucose and 40.6 g/L of xylose and pH thereof was pH 4.5. The medium was collected at predetermined time points and the concentrations of glucose and xylose were measured by HPLC (manufactured by Tosoh Corporation, trade name: LC-8020) and the concentration of ethanol by GC-FID (manufactured by GL Sciences Inc., trade name: GC390B). The results of the measurement of xylose concentration and the ethanol concentration are shown in FIG. 1B.

From FIGS. 1A and 1B, it can be seen that while the xylose concentration hardly changes and the ethanol concentration also does not exceed 40 g/L with the stain N of *Meyerozyma guilliermondii*, the xylose concentration decreases over culture time and the ethanol concentration exceeds 40 g/L with the strain BP-01962.

Therefore, it is apparent that the strain BP-01962 possesses the xylose utilization and ethanol fermentation performance superior to the strain N.

Next, an enzymatically saccharified liquid derived from rice straw treated with 26 mass % ammonia was used as a medium. A liquid culture of the strain BP-01962 was added to the medium to obtain an $OD_{600}$ of 2.0 and cultured at a temperature of 30° C. for 120 hours. The enzymatically saccharified liquid derived from rice straw treated with ammonia contained 73.8 g/L of glucose and 28.3 g/L of xylose and thereof was pH 5.8. The medium was collected at predetermined time points and the concentrations of glucose and xylose were measured by HPLC (manufactured by Tosoh Corporation, trade name: LC-8020) and the concentration of ethanol by GC-FID (manufactured by GL Sciences Inc., trade name: GC390B). The result is shown in FIG. 2.

Figure 2:
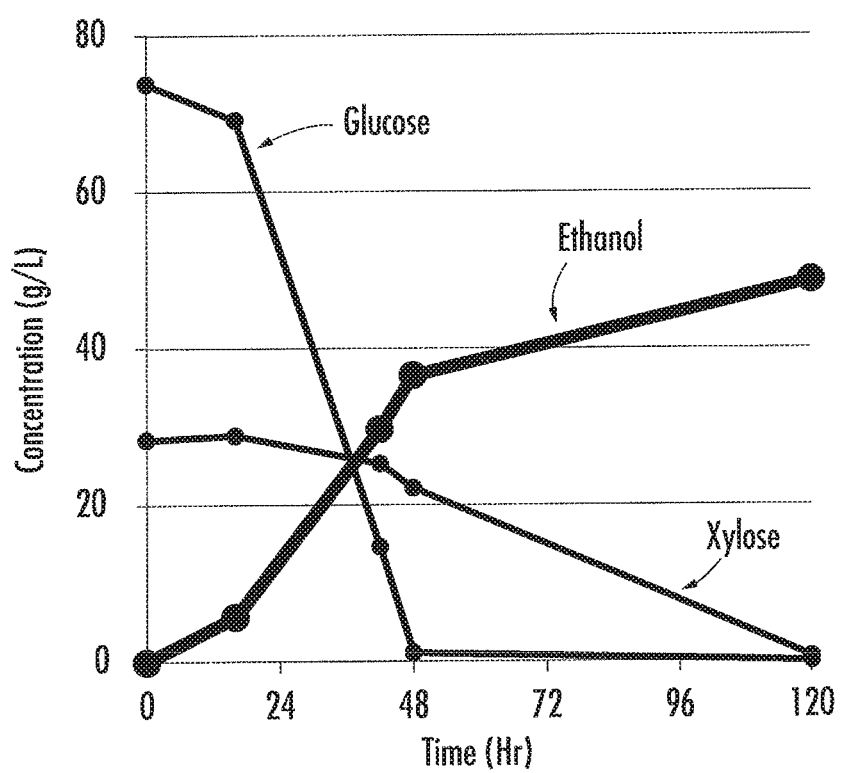
FIG. 2 is a graph illustrating change over time in amount of glucose and xylose digestion and ethanol production by the strain BP-01962 in an enzymatically saccharified liquid derived from rice straw treated with ammonia.

From FIG. 2, it can be seen that the total amount of glucose and xylose has been digested by 120 hours after the onset of culture and the ethanol concentration becomes higher over culture time. Also, since the glucose concentration becomes almost zero by 48 hours after the onset of culturing, but the xylose concentration decreases even after that and the ethanol concentration continues increasing, it is apparent that the strain BP-01962 conducts ethanol fermentation using xylose as substrate after the digestion of the total amount of glucose.

Next, the fermentation yields of the strain N and the strain BP-01962 were compared using an enzymatically saccharified liquid derived from corn stover treated with dilute sulphuric acid.

The enzymatically saccharified liquid derived from corn stover treated with dilute sulphuric acid used was obtained as follows. Corn stover from Iowa, the United States was pretreated by immersing it in 2 volumes of 3.7 mass % sulfuric acid at a temperature of 170° C. for 10 minutes and then returning the temperature to room temperature. Next, to the pretreated corn stover, an NaOH aqueous solution was added to adjust thereof to pH 4 and then a saccharification enzyme (manufactured by Meiji Seika Pharma Co., Ltd., trade name: Acremonium cellulase) was added and enzymatic saccharification was conducted with maintaining the temperature at 50° C. for 72 hours to obtain a slurry containing an enzymatically saccharified liquid. Next, solid-liquid separation of the slurry was conducted by centrifugation and pH of the collected liquid was adjusted to pH 6 with an NaOH aqueous solution; the resultant liquid was used as the aforementioned enzymatically saccharified liquid derived from corn stover treated with dilute sulphuric acid. The enzymatically saccharified liquid derived from corn stover treated with dilute sulphuric acid comprises, for example, 3-15 mass % of glucose and 1-10 mass % of xylose.

Figure 3:
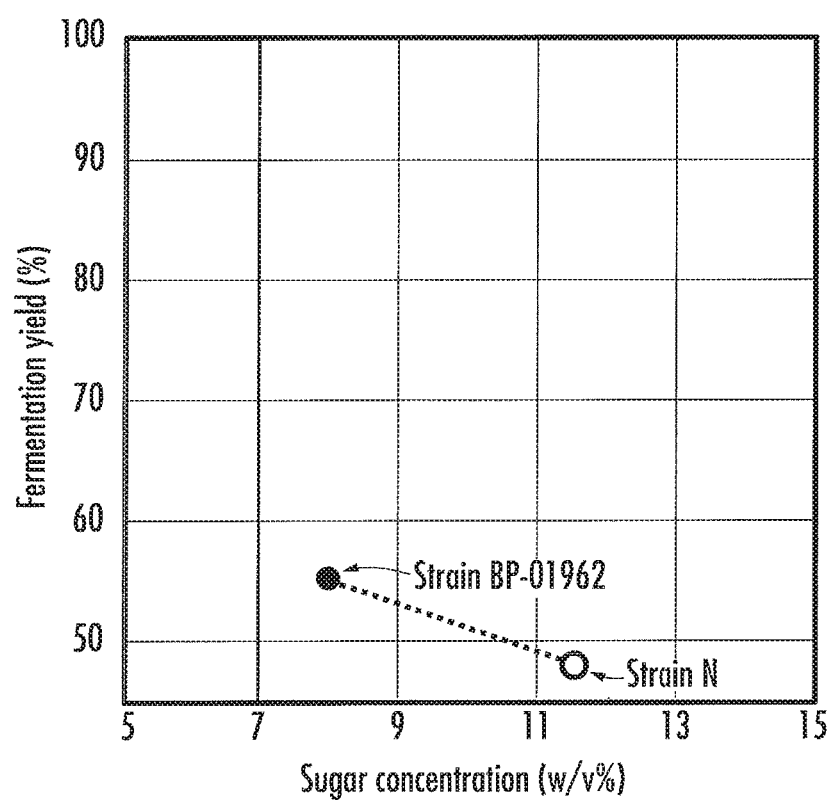
FIG. 3 is a graph illustrating the relation between the sugar concentration and the fermentation yield of the strains BP-01962 and N in an enzymatically saccharified liquid derived from corn stover treated with dilute sulphuric acid.

Next, an enzymatically saccharified liquid derived from corn stover treated with 15 mass % dilute sulphuric acid was used as a medium. A liquid culture of the strain BP-01962 was added to the medium to obtain an $OD_{600}$ of 0.5 and cultured at a temperature of 30° C. for 100 hours. The enzymatically saccharified liquid derived from corn stover treated with dilute sulphuric acid contained 45 g/L of glucose and 38 g/L of xylose and pH thereof was pH 6. After the culture, the medium was collected and the concentration of ethanol was measured by GC-FID (manufactured by GL Sciences Inc., trade name: GC390B) and the fermentation yield was calculated by the following equation (1). The result is shown in FIG. 3.

Fermentation yield=produced ethanol concentration/ (glucose concentration+xylose concentration)/ 0.5114   (1)

(The glucose concentration and the xylose concentration are the initial concentrations before the onset of culturing)

Next, an enzymatically saccharified liquid derived from corn stover treated with 26 mass % dilute sulphuric acid was used as a medium. A liquid culture of the strain N of Meyerozyma guilliermondii was added to the medium to obtain an $OD_{600}$ of 0.5 and cultured at a temperature of 30° C. for 100 hours. The enzymatically saccharified liquid derived from corn stover treated with dilute sulphuric acid contained 64 g/L of glucose and of xylose and pH thereof was pH 6. After the culture, the medium was collected and the concentration of ethanol was measured by GC-FID (manufactured by GL Sciences Inc., trade name: GC390B) and the fermentation yield was calculated by the equation (1). The result is shown in FIG. 3.

From FIG. 3, it is apparent that the strain BP-01962 possesses the ethanol fermentation performance superior to the strain N with the lower concentration of the enzymatically saccharified liquid derived from corn stover treated with dilute sulphuric acid than that used for the strain N.

Next, an enzymatically saccharified liquid derived from corn stover treated with 20 mass % dilute sulphuric acid was used as a medium. Liquid cultures of the strain BP-01962 and the strain N were added to the medium to obtain an $OD_{600}$ of 2.0 and cultured at a temperature of 30° C. for 120 hours. The enzymatically saccharified liquid derived from corn stover treated with dilute sulphuric acid contained 58.8 g/L of glucose and 33.8 g/L of xylose and pH thereof was pH 6. The medium was collected at predetermined time points and the concentration of ethanol was measured by GC-FID (manufactured by GL Sciences Inc., trade name: GC390B). The result is shown in FIG. 4.

Figure 4:
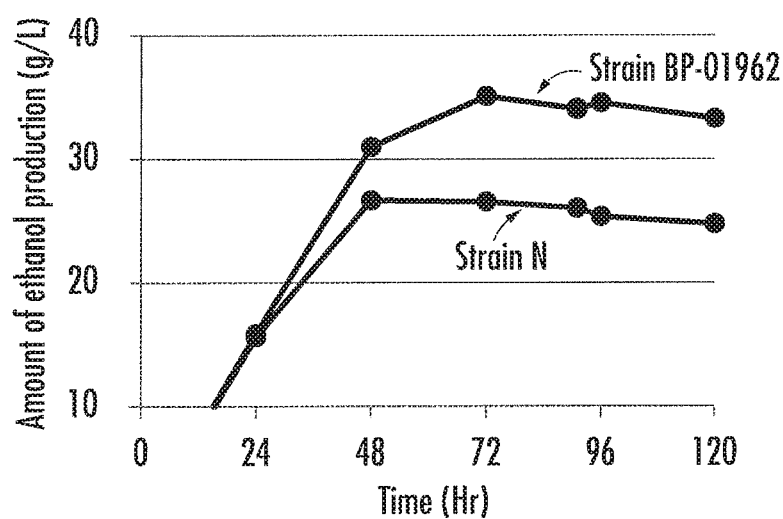
FIG. 4 is a graph illustrating change over time in amount of ethanol production of the strains BP-01962 and N in an enzymatically saccharified liquid derived from corn stover treated with dilute sulphuric acid.

From FIG. 4, it is apparent that the strain BP-01962 also possesses the ethanol fermentation performance superior to that of the strain N with the aforementioned enzymatically saccharified liquid derived from corn stover treated with dilute sulphuric acid at the concentration same as that used for the strain N.

Moreover, the strain BP-01962 was able to produce an approximately equal result in any of cell growth, glucose utilization, xylose utilization, and amount of ethanol production in fermentation when the scale was changed from 1 L, which is a scale of the laboratory level, to 5000 L. Therefore, the strain BP-01962 is also a strain that is useful for industrial production.

REFERENCE SIGN LIST

No reference sign.

The invention claimed is:

1. A highly efficient ethanol-fermentative yeast, the fermentative yeast effectively producing ethanol from pentose and hexose,
 wherein the fermentative yeast has xylose utilization and ethanol fermentation performance improved, in comparison with a wild strain of *Meyerozyma guilliermondii*, by performing habituation of the wild strain of *Meyerozyma guilliermondii* in culture in a medium in which a mutagen is added to an enzymatically saccharified liquid derived from rice straw treated with ammonia, the mutagen including any one of an ethylating agent, a base analog and a nitroso compound, and selecting yeasts growing in the medium and
 wherein the fermentative yeast is deposited to National Institute of Technology and Evaluation (NITE) Patent Microorganisms Depositary under the accession number NITE BP-01962.

2. An ethanol-fermentative yeast deposited to National Institute of Technology and Evaluation (NITE) Patent Microorganisms Depositary under accession number NITE ABP-01962.

* * * * *